United States Patent
Lai et al.

(10) Patent No.: US 9,360,483 B2
(45) Date of Patent: Jun. 7, 2016

(54) CONSTRUCTS AND METHODS TO IDENTIFY ANTIBODIES THAT TARGET GLYCANS

(75) Inventors: Jonathan R. Lai, Bronx, NY (US); Alex Stewart, New York, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 637 days.

(21) Appl. No.: 13/885,203

(22) PCT Filed: Nov. 23, 2011

(86) PCT No.: PCT/US2011/061990
§ 371 (c)(1),
(2), (4) Date: Jul. 1, 2013

(87) PCT Pub. No.: WO2012/074863
PCT Pub. Date: Jun. 7, 2012

(65) Prior Publication Data
US 2013/0281317 A1    Oct. 24, 2013

Related U.S. Application Data

(60) Provisional application No. 61/418,556, filed on Dec. 1, 2010.

(51) Int. Cl.
*C12N 15/13* (2006.01)
*G01N 33/68* (2006.01)
*C12N 15/10* (2006.01)
*C07K 16/10* (2006.01)

(52) U.S. Cl.
CPC ........ *G01N 33/6854* (2013.01); *C07K 16/1063* (2013.01); *C12N 15/1037* (2013.01); *C07K 2317/54* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| 2003/0219839 A1 | 11/2003 | Bowdish et al. |
| 2005/0003347 A1 | 1/2005 | Calabrese et al. |
| 2010/0093563 A1 | 4/2010 | Williamson et al. |

OTHER PUBLICATIONS

PCT International Search Report dated Apr. 10, 2012 in connection with PCT International Patent Application No. PCT/US/2011/061990, 7 pages.
PCT Written Opinion of the International Searching Authority dated Apr. 10, 2012 in connection with PCT International Patent Application No. PCT/US/2011/061990, 5 pages.
Lee C V et al., entitled "Bivalent antibody phage display mimics natural immunoglobulin," Journal of Immunological Methods, 284 (2004), 119-132.
Calarese D A et al., entitled "Antibody Domain Exchange is an Immunological Solution to Carbohyrate Cluster Recognition," Science, vol. 300, Jun. 27, 2003, 2065-2071.
Trkola A et al., entitled "Human monoclonal antibody 2G12 defines a distinctive neutralization epitope on the gp120 glycoprotein of human immunodeficiency virus type 1," Journal of Virology, Feb. 1996, vol. 70, No. 2, 1100-1108.
Stewart A et al., entitled "A strategy for phage display selection of functional domain-exchanged immunoglobulin scaffolds with high affinity for glycan targets," Journal of Immunological Methods, 376 (2012), 150-155.
Liu Y et al., entitled "Synthetic Fab fragments that bind the HIV-1 gp41 heptad repeat regions," Biochemical and Biophysical Research Communications, 413 (2011), 611-15.

*Primary Examiner* — Christopher M Gross
(74) *Attorney, Agent, or Firm* — Amster, Rothstein & Ebenstein LLP

(57) ABSTRACT

Nucleic acid constructs for expressing an antibody on the surface of bacteriophage are disclosed, as are methods for using the constructs to identify antibodies that target glycans.

12 Claims, 9 Drawing Sheets

C

D

CONSTRUCTS AND METHODS TO IDENTIFY ANTIBODIES THAT TARGET GLYCANS

CROSS-REFERENCE TO RELATED APPLICATIONS

This application is a U.S. national stage entry under 35 U.S.C. §371 of PCT International Patent Application No. PCT/US2011/061990, filed Nov. 23, 2011, which claims priority to U.S. Provisional Patent Application No. 61/418,556, filed Dec. 1, 2010, the contents of which are incorporated herein by reference into the subject application.

STATEMENT OF GOVERNMENT SUPPORT

This invention was made with government support under grant number CA155472 awarded by the National Institutes of Health. The government has certain rights in the invention.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

Glycans (oligosaccharides) are critical information carriers in biology, but progress toward understanding their roles has been hampered by lack of reagents that can detect subtle variations in glycan composition [1-4]. Antibodies and glycan-binding proteins (e.g., lectins) that recognize specific terminal sugars on oligosaccharides exist and are widely used, but these reagents have low affinity and are unable to distinguish among branched oligosaccharides [1, 2, 5]. Subtle changes in the glycan composition of cellular surface receptors, which can only be detected by discrimination of chemically similar high molecular weight branched glycans, are thought to signal major cellular events [1-4]. Therefore, reagents that can distinguish branched oligosaccharides from one another would be of high value in glycobiology research [5-12]. Antibodies with these capabilities are difficult to obtain using hybridoma methods because glycans themselves tend to be poorly immunogenic, and it is difficult to target antibody response to regions of oligosaccharides that would allow the desired differentiation [5, 8, 13, 14]. Furthermore, the molecular basis for selective and high-affinity glycan recognition by antibodies is poorly understood—there is much less structural data available for glycan-targeting antibodies than for antibodies that bind proteins [6, 7, 15-17]. Since glycans have much less hydrophobic functionality than do proteins and nucleic acids, glycan-protein interactions tend to be lower affinity than protein-protein or protein-nucleic acid interactions. Changes in cell surface glycan composition are associated with cancer and other disease states; therefore, high-affinity antibodies that target glycans have greater potential as diagnostic and therapeutic delivery agents. In particular, the tetrasaccharide Lewis Y antigen is highly expressed in cancer tissues and a Le$^Y$ antibody-drug conjugate has been advanced through clinical trials [10]. High-affinity glycan antibodies would be important for deciphering glycan function in cancer and other diseases, and would provide a new avenue for the development of diagnostic and therapeutic delivery reagents.

The present invention addresses the need for methods that can be used to identify high-affinity antibodies that target glycans.

SUMMARY OF THE INVENTION

The present invention provides nucleic acid constructs comprising HindIII (AAGCTT), 2G12 VL (SEQ ID NO:1), $C_L$ (SEQ ID NO:2), Intragenic region (SEQ ID NO:3), pel B (SEQ ID NO:4), Region X (SEQ ID 5), spe I (ACTAGT), VH (SEQ ID NO:6), $C_H$ (SEQ ID NO:7), Hinge (SEQ ID NO:8), GCN4 (SEQ ID NO:9), and SalI (GTCGAC), or a modified version thereof wherein the modification consists of one or more modification in the sequence of the 2G12 VL region and/or one or more modification in the sequence of the VH region, and wherein the modification consists of a substitution of one codon for another codon, up to nine such substitutions, and/or insertion of up to nine additional codons.

The invention further provides methods for identifying an antibody that targets a glycan of interest, comprising: a) expressing an antibody encoded by any of the nucleic acid constructs disclosed herein on the surface of bacteriophage; and b) contacting the bacteriophage with the glycan of interest; wherein binding of the glycan to the antibody expressed on the bacteriophage identifies the antibody as an antibody that targets the glycan of interest, and wherein lack of binding of the glycan to the antibody expressed on the bacteriophage indicates that the antibody is not an antibody that targets the glycan of interest.

Hydrogen bonds are shown as dotted lines. Van der Waals or hydrophobic interactions are indicated with an arch.

Figure 6A:
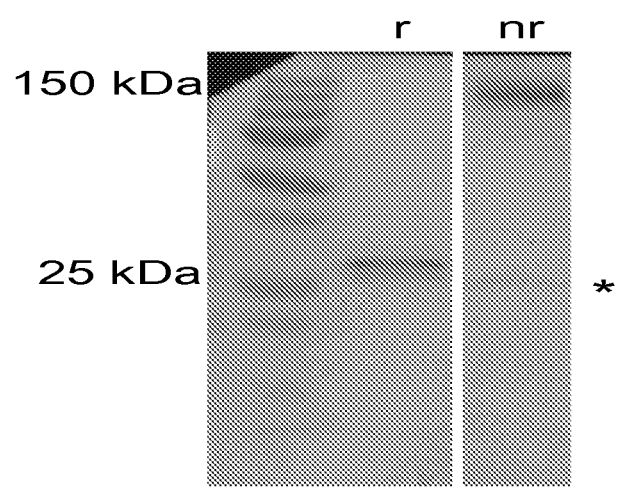
Figure 6B:
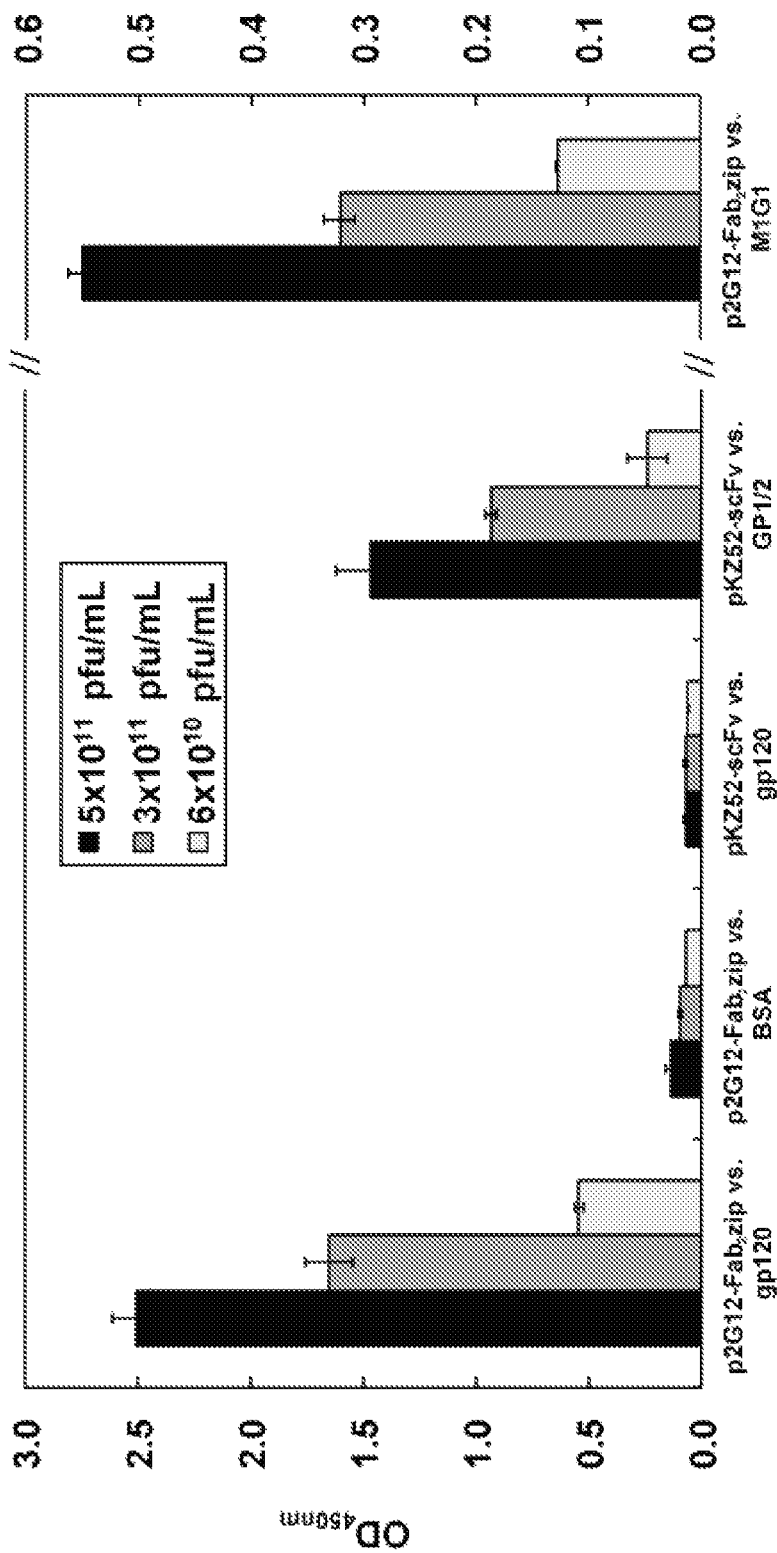

FIG. 6A-6B. Functional expression of the 2G12 (Fab)2 fragment on phage. (A) Western blot analysis of p2G12-Fab2zip phage particles under reducing (r) and non-reducing (nr) conditions using an anti-FLAG/HRP probe (a FLAG epitope is included on the light chain for detection). The asterisk indicates a polyreactive phage protein. (B) Phage ELISA of p2G12-Fab2zip or pKZ52-scFv phage against various targets at three phage titers.

Figure 7:
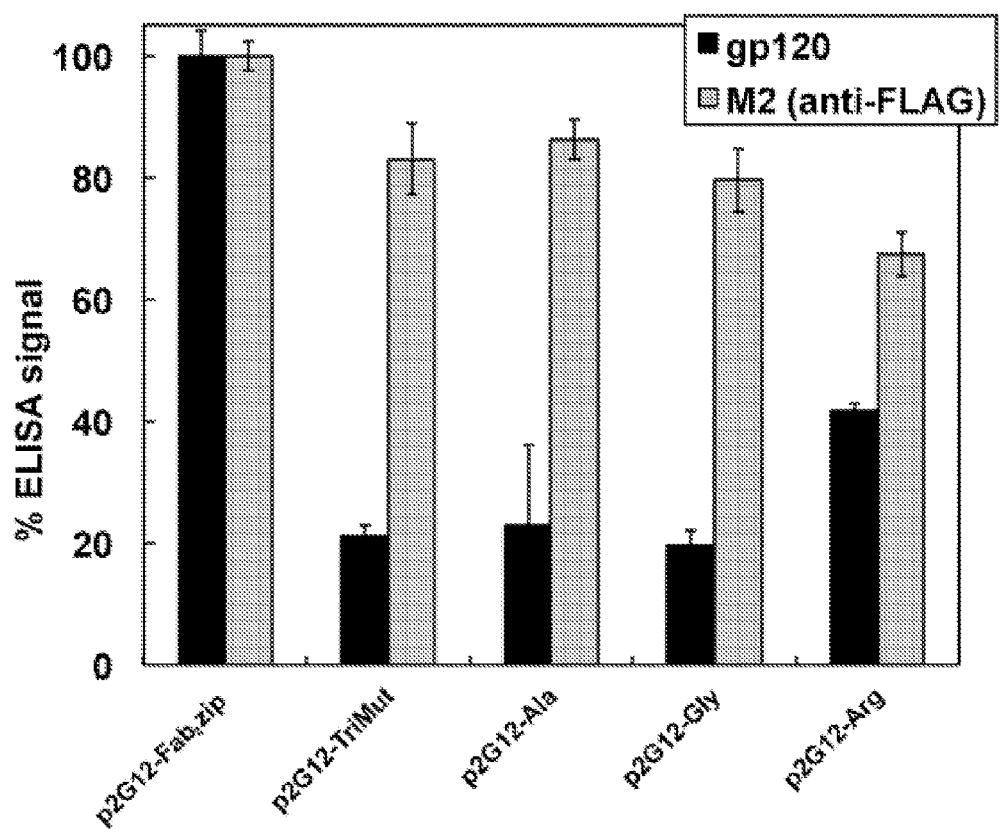

FIG. 7. Comparison of function among p2G12-Fab2zip and mutants. The ELISA binding signal is normalized relative to the WT (p2G12-Fab2zip) signal for both gp120 and anti-FLAG antibody M2.

DETAILED DESCRIPTION OF THE INVENTION

The present invention provides a nucleic acid construct comprising HindIII (AAGCTT), 2G12 VL (SEQ ID NO:1), $C_L$ (SEQ ID NO:2), Intragenic region (SEQ ID NO:3), pel B (SEQ ID NO:4), Region X (SEQ ID 5), spe I (ACTAGT), VH (SEQ ID NO:6), $C_H$ (SEQ ID NO:7), Hinge (SEQ ID NO:8), GCN4 (SEQ ID NO:9), and SalI (GTCGAC), or a modified version thereof, wherein the modifications consists of one or more modification in the sequence of the 2G12 VL region and/or one or more modification in the sequence of the VH region, and wherein the modifications consists of a substitution of one codon for another codon, up to nine such substitutions, and/or insertion of up to nine additional codons.

As used herein, a "codon" refers to three adjacent nucleotides that specifies the genetic code information for synthesizing a particular amino acid.

One embodiment comprises one or more modifications in the sequence of the 2G12 VL region. In a preferred embodiment, the region that is modified is the "TAC" at nucleotides 277-279 of SEQ ID NO:1 as indicated by underlining below:

(SEQ ID NO: 1)
GTTGTTATGACCCAGTCTCCGTCTACCCTGTCTGCTTCTGTTGGTGACAC

CATCACCATCACCTGCCGTGCTTCTCAGTCTATCGAAACCTGGCTGGCTT

GGTACCAGCAGAAACCGGGTAAAGCTCCGAAACTGCTGATCTACAAAGCG

TCTACTCTGAAAACCGGTGTTCCGTCTCGTTTCAGCGGTTCTGGTTCTGG

TACTGAGTTCACCCTGACCATCTCTGGTCTGCAGTTCGACGACTTCGCTA

CCTACCACTGCCAGCACTACGCTGGTTACTCTGCTACCTTCGGCCAGGGT

ACCCGTGTAGAAATCAAACGT.

One embodiment comprises one or more modifications in the sequence of the VH region. In a preferred embodiment, the region that is modified includes one or more of the "CGT" at nucleotides 81-83, the "CTGGAAGAC" at nucleotides 223-231, and/or the GAC" and nucleotides 316-318 of SEQ ID NO:6 as indicated by underlining below:

(SEQ ID NO: 6)
GAAGTTCAGCTGGTTGAAAGCGGCGGCGGTCTGGTTAAAGCTGGCGGTTC

TCTGATCCTGTCTTGCGGTGTTTCTAACTTCCGTATCTCTGCTCACACCA

TGAACTGGGTTCGTCGTGTTCCGGGCGGAGGTCTGGAATGGGTTGCTTCT

ATCTCTACCTCTTCCACCTACCGTGACTATGCTGACGCTGTTAAAGGTCG

TTTCACCGTTTCTCGTGACGACCTGGAAGACTTCGTTTACCTGCAGATGC

ACAAAATGCGTGTTGAAGACACCGCTATCTACTACTGCGCTCGTAAAGGT

TCTGACCGTCTGTCTGACAACGACCCGTTCGACGCTTGGGGTCCGGGCAC

CGTTGTTACCGTAAGCCCG.

Another embodiment comprises one or more modification in the sequence of the 2G12 VL region and one or more modification in the sequence of the VH region.

The codon that is added to, or substituted in, the sequence of the VL and/or VH region can be, for example, one or more of NNS, DVK, WNY, KVK, KMT and TMT, where N=A/T/C/G, S=G/C, D=A/G/T, V=A/C/G, K=G/T, W=A/T, Y=C/T, and M=A/C, where, for example, "A/C" means nucleotide A or nucleotide C.

The modification, for example, can consist of a substitution of 1, 2, 3, 4, 5, 6, 7, 8 or 9 codons in the sequence of the VL region. As another example, the modification can consist of a substitution of 1, 2, 3, 4, 5, 6, 7, 8 or 9 codons in the sequence of the VH region. As a further example, the modification can consist of a substitution of 1, 2, 3, 4, 5, 6, 7, 8 or 9 codons in the sequence of the VL region and in the VH region, for a total of up to 9 substitutions. Additionally, or alternatively, the modification can consist of insertion of 1, 2, 3, 4, 5, 6, 7, 8 or 9 additional codons in the VL region, or in the VH region, or in VL region and in the VH region, up to an insertion of a total of nine additional codons. The insertion of multiple codons can occur at the same position in the sequence or at different positions in the sequence. The same codon can be inserted, and/or substituted, at one or more locations.

The invention further provides a method for identifying an antibody that targets a glycan of interest, comprising:

a) expressing an antibody encoded by any of the nucleic acid constructs disclosed herein on the surface of bacteriophage; and b) contacting the bacteriophage with the glycan of interest;

wherein binding of the glycan to the antibody expressed on the bacteriophage identifies the antibody as an antibody that targets the glycan of interest, and wherein lack of binding of the glycan to the antibody expressed on the bacteriophage indicates that the antibody is not an antibody that targets the glycan of interest.

The bacteriophage can be, for example, a M13, fd filamentous phage, T4, T7 or λ bacteriophage, and is preferably a M13 bacteriophage.

The glycan is preferably immobilized to a fixed surface. For example, the glycan can be biotinylated and the fixed surface can be a streptavidin-coated surface.

The glycan of interest can be any glycan. Preferred examples include the oligomannose sugars on HIV-1 gp120, and Le$^Y$ antigen.

Preferably, the antibody that is identified binds the glycan with a $K_D$ of 50 nM or lower.

The invention further provides an antibody that targets a glycan of interest, wherein the antibody is identified by any of the methods disclosed herein.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

Figure 1:
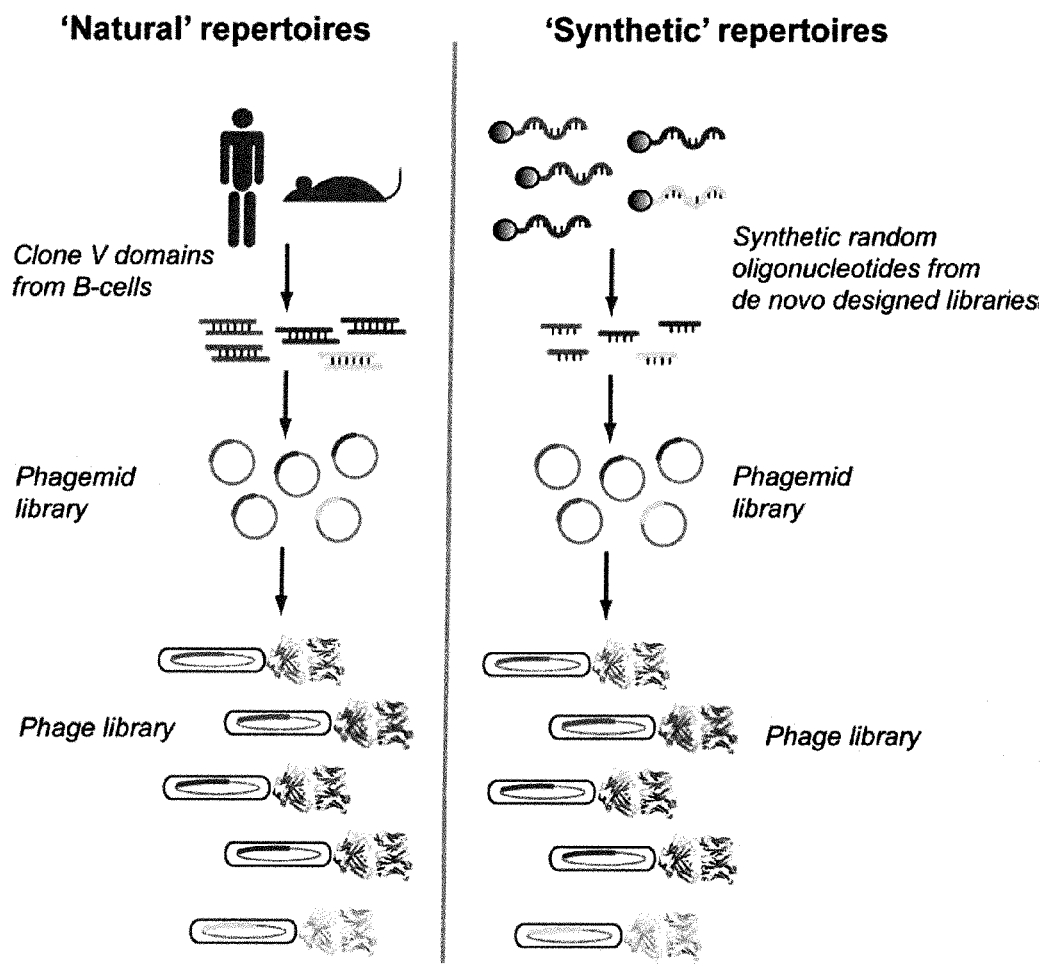
FIG. 1. Antibody phage display libraries bearing 'natural' and 'synthetic' diversity.

In the present approach, a recently-developed phage display technology ('synthetic antibody' technology) is applied to the development of novel methods for the identification of high-affinity glycan-specific antibodies [18-23]. The expression and selection of antibody fragments on the surface of bacteriophage was first reported nearly two decades ago, but most antibody phage display methods rely on cloning V domain diversity from human or animal sources ('natural' repertoires in FIG. 1) [18]. This requirement presents a significant obstacle for identification of glycan-specific antibodies since endogenous glycans are poorly immunogenic—thus, antibodies with combining site features that are biased toward high-affinity glycan interactions may not be adequately represented among such libraries. Furthermore, the few naturally occurring glycan antibodies that have been well characterized exhibit relatively modest binding affinity, which limits their utility [5-8, 14-17].

The 'synthetic antibody' approach is not dependent on natural source repertoires for variable domain diversity ('synthetic' repertoires in FIG. 1) [18-24]. Instead, combined bioinformatic/structural studies on known antibodies, and empirical observations from phage display libraries, guide the design of minimal diversity codon sets that encode amino acids containing physicochemical properties biased toward antibody-antigen interactions [18, 23]. The diversity (targeted to the antibody complementarity determining regions, CDRs) is encoded by designed, synthetic oligonucleotides (thus, 'synthetic antibodies'). Therefore, generation of these libraries is not dependent on repertoires of naturally-occurring antibodies. Over the past five years, several groups have defined optimal codon sets for generation of specific and high-affinity synthetic antibodies targeting protein and peptide antigens [18-24]. In a recent iteration of this work, libraries in which CDR positions were varied to allow a binomial Tyr/Ser randomization scheme yielded specific antibodies against several different protein targets [20]. Minimization of amino acid diversity permitted at CDR positions decreases the maximum theoretical diversity (i.e., the total possible number of sequences in the library) and therefore allows higher sampling with phage display methods (typical phage display libraries range from $10^8$-$10^{10}$ total clones). This strategy has been successful for protein and peptide antigens but no such methodology exists for glycan antibodies [18-24].

Vector Construction and Mutagenesis

The bivalent Fab display phagemid pAS-Fab2zip was modified to generate bivalent 2G12 Fab phagemid (p2G12-Fab2zip). Splice overlap extension polymerase chain reaction was performed to generate a DNA fragment containing the 2G12 light chain variable and constant domains (VL and CL, respectively) and the heavy chain variable and constant domains (VH and CH, respectively), which were subcloned into pAS-Fab2zip. Kunkel mutagenesis was performed to generate mutants of p2G12-Fab2zip (p2G12-Ala, and p2G12-Gly). Briefly, single-stranded, uridine-enriched DNA (ss-dU-DNA) of p2G12-Fab2zip was prepared in *E. coli* CJ236 cells (New England Biolabs, Ipswich, Mass.) using standard protocols. Kunkel mutagenesis was performed using 5'-phosphorylated primers containing the desired mutations. Typical Kunkel mutagenesis reactions contained 3-5 μg of ss-dU-DNA, a four-fold excess of mutagenesis primer, three units of T4 DNA polymerase (New England Biolabs), and two units of T4 ligase (Invitrogen, Carlsbad, Calif.). Reaction components were mixed and incubated at room temperature overnight and the products purified using a QIAgen (Valencia, Calif.) PCR purification kit. For the triple mutant p2G12-TriMut, a synthetic DNA fragment encoding the heavy chain fragment with mutations was obtained from a commercial supplier (Genewiz, South Plainfield, N.J.) and subcloned as above.

Phage Display

*E. coli* XL1-Blue (Stratagene Agilent Technologies, Santa Clara, Calif.) harboring p2G12-Fab2zip were grown for ~4 hrs in 2×YT broth supplemented with 5 μg/mL tetracycline and 50 μg/mL carbenicillin at 37° C. Helper phage M13-K07 (NEB, Ipswich, Mass.) were added to ~$10^{10}$ plaque-forming units (pfu)/mL, followed by 25 μg/mL kanamycin. The culture was grown for 16-18 hrs at 30° C., the cells removed by centrifugation, and phage precipitated by addition of 3% (w/v) NaCl and 4% (w/v) PEG 8000. The phage were pelleted by centrifugation and resuspended in phosphate-buffered saline/0.05% (v/v) Tween 20 (PBS-T) containing 0.5% (w/v) BSA. Expression of an irrelevant bivalently displayed single chain variable fragment (scFv, pKZ52-scFv2zip) was similar except the expression culture was grown at 37° C.

Western Blots

The p2G12-Fab2zip phage (~$10^{11}$ pfu/ml) were denatured by incubation at 100° C. for 10 mins in SDS-PAGE buffer with or without β-mercaptoethanol (BME). The solution containing denatured phage particles was run on a 10% Trisglycine HCl SDS-PAGE polyacrylamide gel and subsequently electrotransferred to polyvinylidene fluoride (PVDF) filter paper. Next, the filter paper was blocked with blocking buffer (Sigma, St. Louis, Mo.) for 10 mins and then incubated with an anti-FLAG/horseradish peroxidase (HRP) conjugate (Sigma) in a 1:2500 dilution from stock in the blocking buffer for 1 hr. The filter paper was washed five times with Tris-buffered saline containing 0.05% (v/v) Tween 20 (TBS-T) and developed with ECL development solution (Pierce/Thermofisher Scientific, Rockville, Ill.). The blot was visualized on a on a GE ImageQuant LAS 4000.

Phage Enzyme-Linked Immunosorbent Assay (ELISA)

Wells of Costar EIA/RIA high-binding plates were coated with ~400-600 μg of antigen per well in phosphate-buffered saline (PBS) pH 7.0 at room temperature for 1 hr. The well solutions were decanted, and unbound well sites were blocked with PBS-T/0.5% (w/v) BSA for 1 hr. The wells were washed with PBS-T, phage solutions added and allowed to bind for 30 mins. The phage solutions were decanted, the wells washed 5-7 times with PBS-T. Next, a solution containing 1:2500 dilution of anti-M13/HRP conjugate (GE Healthcare, Piscataway, N.J.) was added and allowed to bind for 30 mins. The wells were washed with PBS-T ~5-7 times and developed using 3,3',5,5'-tetramethylbezidine (TMB) substrate (Sigma). The ELISA signal was quantified either by direct measurement of blue color absorbance (OD650) or by quenching with sulfuric acid after 10-15 mins and determining the OD at 450 nm.

Mock Selections

Phage cultures containing mutations at selected contact residues at the HCDR1 and HCDR3 regions (p2G12-Ala, p2G12-Gly, p2G12-Arg) were spiked with small amounts of p2G12-Fab2zip phage to produce input phage populations for the mock selection. The ratios of WT (p2G12-Fab2zip) and mutant (p2G12-Ala and p2G12-Gly) in each input population were assessed by large-scale DNA sequencing. In all three input populations, the WT to mutant ratios (p2G12-Fab2zip: p2G12-Ala and p2G12-Fab2zip:p2G12-Gly) were less than 1:50. These spiked input populations were subjected to a single round of mock selection. The protein target gp120 was immobilized in wells of Costar EIA/RIA as above. Solution containing the input phage population was added and allowed to bind for 1-2 hrs. Next, the wells were washed ~5-7 times with PBS-T. Treatment with 100 µL of 100 mM glycine HCl pH 2.1 to each well for 10 mins allowed for elution of phage. Subsequently, the solution neutralized by addition to 50 µL of 2M Tris, pH 8. The p2G12-Fab2zip:p2G12-Ala and p2G12-Fab2zip:p2G12-Gly ratios of output populations were assessed by large scale sequencing.

Scaffold for Glycan Synthetic Antibody Discovery

Figures 2A, 2B, 2C:
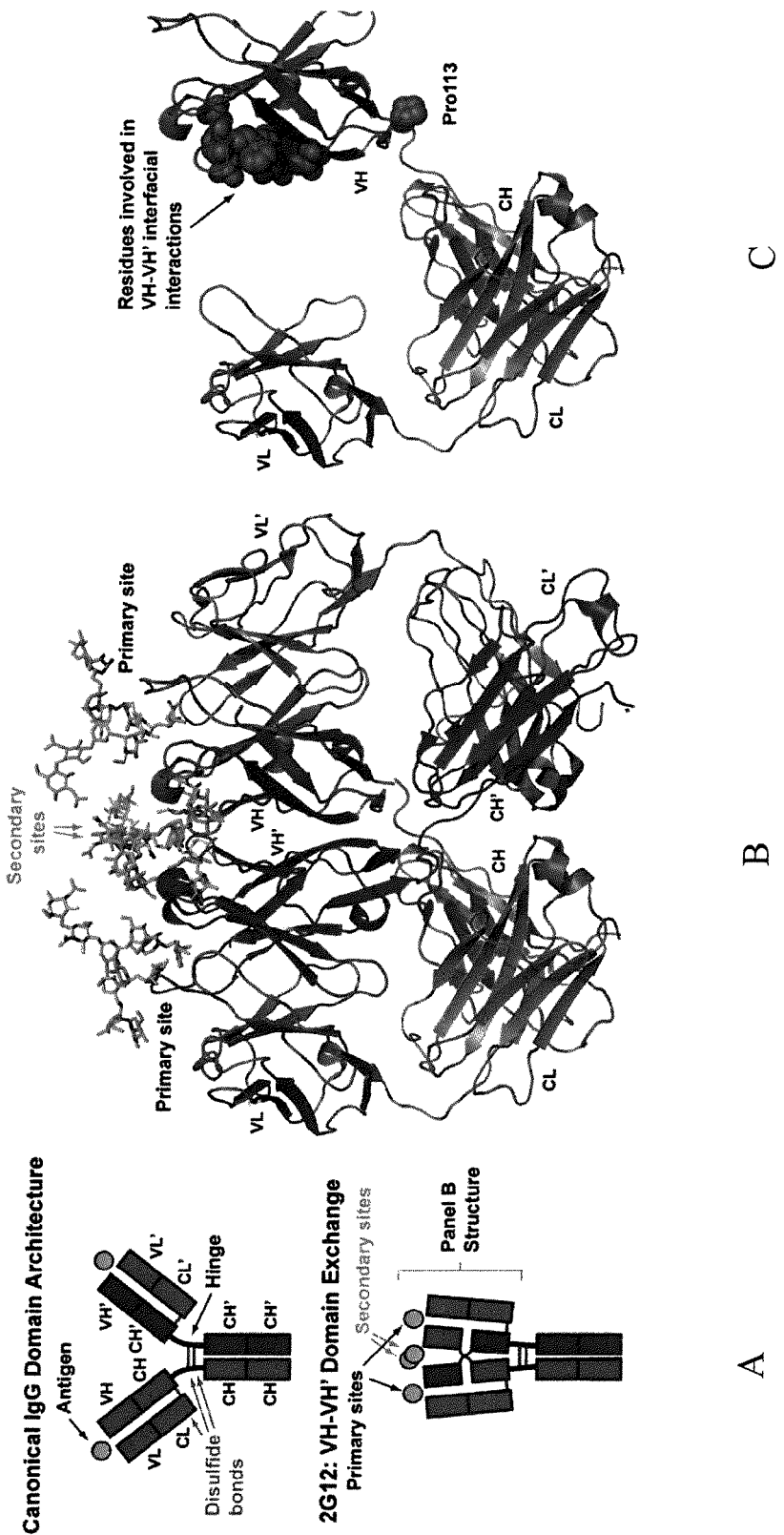
FIG. 2A-2C. Unusual domain-exchange architecture of 2G12. (A) Schematic of domain architecture for canonical IgG molecules (top) and 2G12 (bottom). Canonical IgG architecture results in two antigen binding sites at the interface of light and heavy chain variable domains (VL-VH and VL'-VH'). The VH-VH' domain exchange in 2G12 creates an extended antigen binding surface that contains two additional binding sites at the VH-VH' interface. (B) Crystal structure of the 2G12 Fab dimer in complex with Man$_9$GlcNAc$_2$. (C) Fab monomer of 2G12 showing features that stabilize the domain exchange.

The unique domain-exchange structure of HIV-1 antibody 2G12 provides an immunological solution to high-affinity glycan binding. Since glycans contain much less hydrophobic functionality than do proteins or nucleic acids, individual glycan-protein interactions tend to be much weaker than protein-protein or protein-nucleic acid interactions [1-4]. The HIV-1 neutralizing antibody 2G12 is perhaps the only known example of a high-affinity humoral response to carbohydrate cluster recognition [25, 26]. This antibody binds high molecular weight oligomannose N-glycans on the HIV-1 envelope glycoprotein gp120 with nanomolar affinity [25, 26]; most other glycan antibodies bind with dissociation constants in the micromolar range [5-7, 14-17]. The unusually tight binding of 2G12 results from a unique domain exchange architecture that produces an extended antigen (glycan) interaction surface on the antibody [25]. FIG. 2A shows a schematic for the domain-exchange architecture of 2G12—the only known example in which such a dramatic adaptation of the IgG scaffold is afforded by somatic hypermutation and clonal selection. The crystal structure of the antigen binding fragment (Fab) for 2G12, a dimer, is shown in FIG. 2B complexed with four $Man_9GlcNAc_2$ oligosaccharides (the glycan found on gp120) [25]. The basis for the domain exchange is rooted in a Ser→Pro mutation in the linker region between heavy chain variable and constant domains (VH and CH), which redirects the polypeptide chain in such a manner to promote the exchange of VH and VH' domains on adjacent arms of the IgG molecule (FIG. 2C). An extensive network of interactions among the VH and VH' domains provide additional stabilization for the domain exchange. This unique architecture supports key structural features that endow 2G12 with its rare ability to recognize branched glycans in high affinity. In 2G12, the domain VH-VH' domain exchange results in four glycan-binding pockets per IgG molecule [25]. Two of these glycan binding pockets, the primary binding sites, are located at the VL-VH' and VL'-VH interfaces (FIGS. 2A and 2B). These primary sites correspond to conventional antibody combining sites. Two secondary glycan-binding pockets, diametrically opposed, lie at the VH-VH' interface. This efficient and compact polyvalency, embedded within a single IgG molecule, form the basis for 2G12's ability to form high-affinity interactions with glycan moieties. Furthermore, due to an extended network of contacts with the glycan, 2G12 is able to discriminate $Man_9GlcNAc_2$ from other closely-related oligomannoses [26, 27].

Functional Expression of 2G12 on the Surface of M13 Bacteriophage by Bivalent Fab Display Standard antibody phage display formats rely on monovalent display of Fabs or single chain variable fragments (scFvs) fused to the minor coat protein pIII (one Fab or scFv per phage particle) [28]. These formats would not allow display of the dimeric domain-exchange 2G12 architecture, and therefore a system for functional display of the 2G12 Fab dimmer was engineered. A scFv phagemid display vector was modified (pAPIII6) for display of two Fabs linked by a disulfide-bonded IgG hinge region ('bivalent' Fab display, FIG. 3A) [29, 30]. The bivalent display vector contains two open reading frames (ORFs): one that encodes the entire light chain (variable and constant domains, VL-CL); and another that consists of a fusion between the variable and constant domains of the heavy chain, the IgG hinge region (which contains two disulfide crosslinks), a dimeric GCN4 leucine zipper, and the C-terminal 188 residues of pIII (VH-CH-hinge-GCN4-pIII-CT). It was reasoned that phage assembly upon coinfection with helper phage would lead to display of two Fabs on each phage particle, linked by the hinge region disulfide bonds (FIG. 3B) [30]. The GCN4 leucine zipper promotes dimer formation during the phage assembly process. A FLAG sequence was fused to the light chain N-terminus for detection purposes. A ribosome binding site (RBS) was included in the region between the two ORFs, and light chain and the heavy chain fusion protein contain OmpA and PelIB leader sequences (respectively) for export to the host periplasm during phage production. The DNA was assembled for this bivalent display vector, which was termed pAPIII6-$(Fab)_2$-zip, from synthetic DNA fragments.

Open Reading Frames

Open reading frames (ORFs) of the Nucleic Acid Construct are shown below.

```
HindIII (artificial sequence, cloning site)
AAGCTT

2G12 VL (artificial sequence, encodes human VL)
                                          (SEQ ID NO: 1)
GTTGTTATGACCCAGTCTCCGTCTACCCTGTCTGCTTCTGTTGGTGACA

CCATCACCATCACCTGCCGTGCTTCTCAGTCTATCGAAACCTGGCTGGC

TTGGTACCAGCAGAAACCGGGTAAAGCTCCGAAACTGCTGATCTACAAA

GCGTCTACTCTGAAAACCGGTGTTCCGTCTCGTTTCAGCGGTTCTGGTT

CTGGTACTGAGTTCACCCTGACCATCTCTGGTCTGCAGTTCGACGACTT

CGCTACCTACCACTGCCAGCACTACGCTGGTTACTCTGCTACCTTCGGC

CAGGGTACCCGTGTAGAAATCAAACGT

C_L (artificial sequence)
                                          (SEQ ID NO: 2)
ACTGTTGCTGCACCTTCTGTCTTTATCTTTCCTCCGTCCGATGAACAAT

TGAAGAGCGGCACGGCGTCTGTGGTTTGCCTGCTGAATAACTTTTATCC

GCGTGAGGCGAAGGTCCAATGGAAAGTTGATAATGCGCTGCAAAGCGGT

AACAGCCAAGAGTCTGTCACCGAGCAAGACAGCAAAGACAGCACCTACT

CTCTGTCCAGCACCCTGACGCTGAGCAAAGCAGATTACGAGAAACATAA

GGTTTATGCATGTGAAGTTACCCACCAGGGTCTGAGCAGCCCGGTTACC

AAATCTTTTAACCGTGGTGAGTGTTAA

Intragenic region (artificial sequence)
                                          (SEQ ID NO: 3)
TTCTAGATAATTAATTAGGAGGAATTTAAA pel B (artificial sequence)
                                          (SEQ ID NO: 4)
ATGAAATACCTATTGCCTACGGCAGCCGCTGGATTGTTATTACTCGCTG

CCCAACCAGCCATG

Region X (artificial sequence)
                                          (SEQ ID NO: 5)
GCCGAGGTGCAGCTG spe I (artificial sequence)
ACTAGT VH (artificial sequence, encodes human VH)
                                          (SEQ ID NO: 6)
GAAGTTCAGCTGGTTGAAAGCGGCGGCGGTCTGGTTAAAGCTGGCGGTT

CTCTGATCCTGTCTTGCGGTGTTTCTAACTTCCGTATCTCTGCTCACAC

CATGAACTGGGTTCGTCGTGTTCCGGGCGGAGGTCTGGAATGGGTTGCT
```

```
-continued
TCTATCTCTACCTCTTCCACCTACCGTGACTATGCTGACGCTGTTAAAG

GTCGTTTCACCGTTTCTCGTGACGACCTGGAAGACTTCGTTTACCTGCA

GATGCACAAAATGCGTGTTGAAGACACCGCTATCTACTACTGCGCTCGT

AAAGGTTCTGACCGTCTGTCTGACAACGACCCGTTCGACGCTTGGGGTC

CGGGCACCGTTGTTACCGTAAGCCCG

C_H (artificial sequence)
                                              (SEQ ID NO: 7)
GCCAGCACGAAAGGCCCGAGCGTGTTCCCGCTGGCACCGTCGAGCAAAT

CTACCTCCGGTGGCACCGCAGCTCTGGGTTGTCTGGTTAAGGACTACTT

CCCGGAACCTGTTACCGTGAGCTGGAACAGCGGTGCACTGACCTCTGGT

GTCCACACCTTCCCAGCAGTGTTGCAGAGCAGCGGTCTGTATAGCCTGA

GCAGCGTTGTGACGGTTCCTAGCAGCAGCCTGGGTACGCAGACCTATAT

CTGCAACGTGAATCACAAGCCGAGCAACACCAAAGTTGACAAAAAGGTC

GAGCCAAAAGCTGTGATAAGGAGCTC

Hinge (artificial sequence)
                                              (SEQ ID NO: 8)
ACCTGTCCGCCTTGCCCTGCGCCGGAACTGCTGGGC GCN4 (artificial sequence)
                                              (SEQ ID NO: 9)
GGTCGTATGAAACAACTGGAGGACAAGGTCGAGGAGTTGTTGAGCAAGA

ACTACCATCTGGAGAACGAAGTGGCGCGTCTGAAGAAACTGGTTGGTGA

ACGT

SalI (artificial sequence, cloning site)
GTCGAC
```

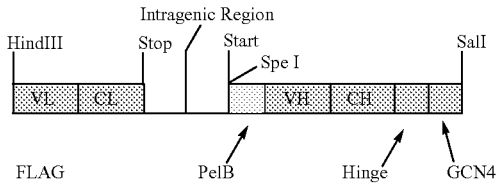

Cloning of 2G12 DNA

The DNA sequence for 2G12 was designed, and then chemically synthesized in fragments by commercial suppliers (DNA 2.0 and Genewiz). The bivalent 2G12 phage expression system was then assembled using a process called 'fragment assembly'. In this method, the fragments of the 2G12 DNA were put together by sequential polymerase chain reaction (PCR) steps. The final product contained cloning sites on either end ('HindIII' and 'SalI') for cloning into the vector known as pAPIII6. This vector (known as a 'phagemid') permits the expression of sequences on the surface of M13 bacteriophage (phage display). The 2G12 DNA was cloned into pAPIII6 by cutting the 2G12 DNA and the pAPIII6 phagemid each with the restriction enzymes HindIII and SalI independently. The 'cut' DNA samples were then purified using a kit supplied by a commercial manufacturer (PCR purification kit, QIAgen). The cut, purified DNA samples of 2G12 and pAPIII6 were mixed, then the enzyme known as 'T4 ligase' (supplied by Promega) was added to the mixture. The samples were then electroporated in E. coli and individual colonies harboring the resulting DNA were grown and screened for the correct product. The correct product was confirmed by DNA sequence analysis.

Protocol for 2G12 Phage Production

The phagemid containing the 2G12 DNA was electroporated into the E. coli cell line 'XL-1 Blue' (a host for M13 bacteriophage production). After recovery, the cells were grown at 37° C. for 1 hour in 2×YT broth media containing tetracycline (an antibiotic to promote growth of cells susceptible to phage infection) and carbenicillin (an antibiotic to select for the cells containing the phagemid) in a 250 mL baffled flask. Next, 4 ml of 2×YT broth media containing second antibiotic (carbenicillin, to select for cells containing the phagemid) as well as a second phage clone (known as a 'helper phage') was then added. The culture was grown for an additional 2 hours, then 25 mL of 2×YT broth media containing carbenicllin and a third antibiotic (kanamycin) was added to select for bacteria that were infected with the helper phage and 2G12 containing phagemid. The culture was then grown at 30° C. overnight. The next day, cells were removed by centrifugation. To the supernatant, sodium chloride and polyethylene glycol 8000 were added to precipitate the phage particles. The mixture was incubated on ice for 45-60 minutes. The precipitate phage were isolated by centrifugation. The phage pellet was redissolved in a solution containing sodium phosphate, sodium chloride, the detergent Tween-20, and the protein bovine serum albumin (BSA). This phage solution was used directly for binding studies. A second protocol was used to prepare the 2G12 phage in some cases; this protocol was similar except that existing 2G12 phage were used to 'infect' the E. coli XL-1 Blue culture as a starting point rather than electroporation. All other steps were the same. In a more recent variation of the procedure, culture was grown in 50 mL falcon tube (Corning) instead of a 250 mL baffled flask, and the precipitated phage was resuspended in a solution containing sodium phosphate, sodium chloride, and BSA.

Two strategies were tried to optimize 2G12 expression: (i) altering the growth conditions for the phage culture; and (ii) altering the phagemid (the 2G12 coding region was kept the same). Neither strategy was successful. Attempts to optimize 2G12 expression included altered growth conditions including different growth temperatures (27° C. and 37° C.), different media conditions (LB, 2×LB, and 2×YT), and different growth times (18 h, 20 h, 24 h) and altering the phagemid (the entire 2G12 DNA segment was subcloned out of the phagemid and inserted it into a different phagemid).

Figure 3A:
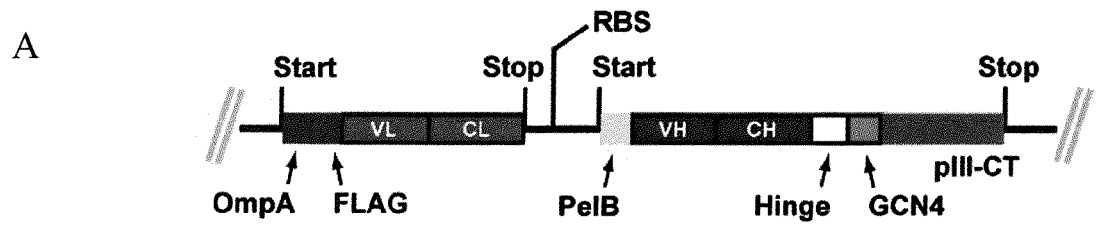
FIG. 3A-3D. Design and evaluation of pAPIII6-(Fab)$_2$-zip for bivalent Fab display. (A) Relevant coding region of the pAPIII6-(Fab)$_2$-zip vector. (B) Phage production results in display of a bivalent assembly that contains two Fabs. Disulfides link the CL and CH, and the two Fabs at the hinge region. The GCN4 drives dimerization during phage assembly. (C) Western blot analysis of whole phage particles using an anti-FLAG/peroxidase probe under nonreducing conditions. A band corresponding to the large bivalent assembly (~150 kDa) is observed in pAPIII6-Fab$_2$-zipΦ but not with control phage bearing no pIII fusion (VCSM13). The band at 25 kDa is a polyreactive phage protein. (D) Phage ELISA showing binding of pAPIII6-Fab$_2$-zipΦ to biotinylated VEGF (bVEGF) immobilized to a streptavidin-coated surface but not to BSA. No binding of VCSM13 control phage to bVEGF was observed.
Figure 3B:
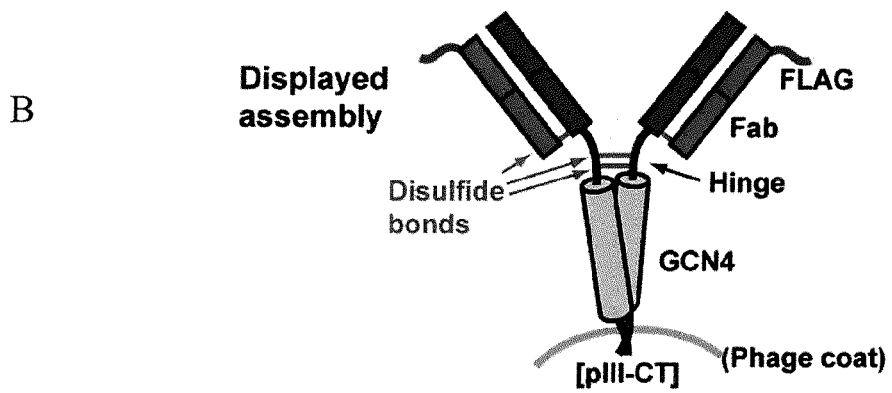
Figure 3C:
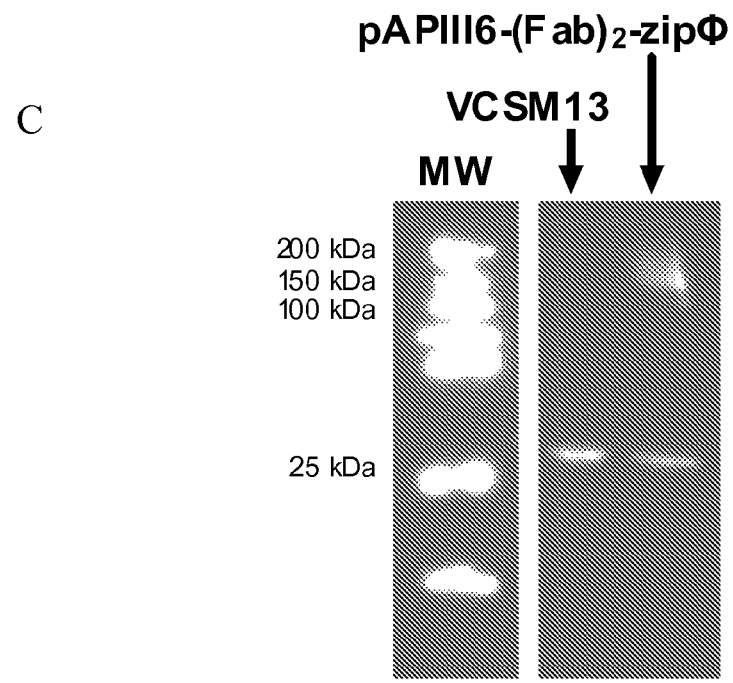
Figure 3D:
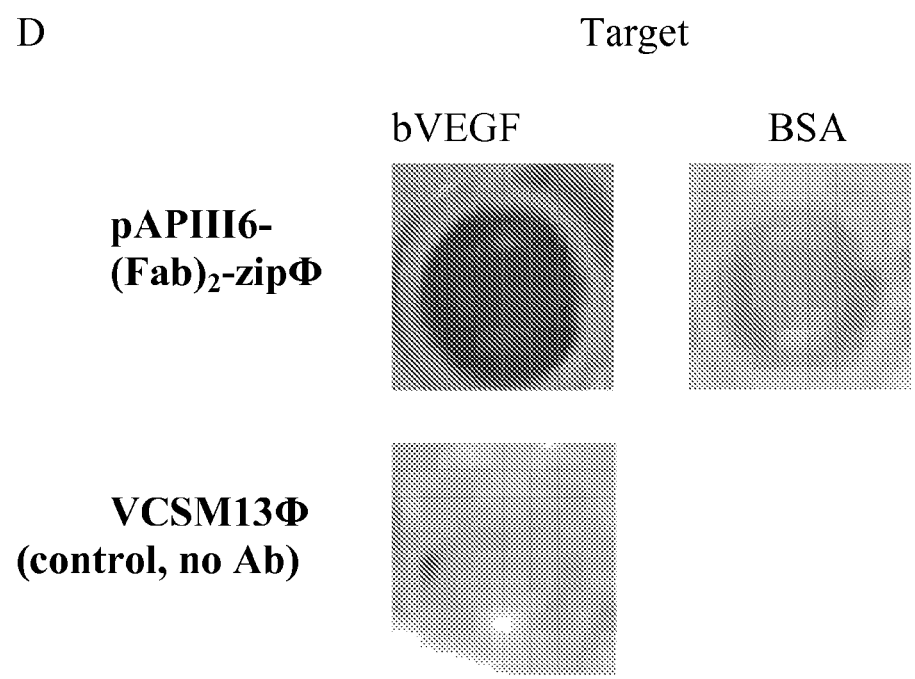

Functional Expression of 2G12 on the Surface of M13 Bacteriophage by Bivalent Fab Display As a test case, VL and VH were cloned from a known antibody that targets vascular endothelial growth factor (VEGF) and the corresponding phage particles (pAPIII6-Fab$_2$-zipΦ) were produced. The bivalent nature of the Fab display was validated by Western blot analysis. Under non-reducing conditions, the entire bivalent assembly (~150 kDa) remains intact and should therefore be detectable with an anti-FLAG/peroxidase probe (a FLAG epitope is located at the VL N-terminus) (FIG. 3A). As shown in FIG. 3C, the 150 kDa bivalent assembly was observed. To ensure that this band arises from the bivalent assembly, replicate Western blot analysis was performed with two other probes: (i) an anti-pIII/peroxidase probe that recognizes the M13 minor coat protein; and (ii) an anti-κ-light chain/peroxidase probe that recognizes conserved portions of the VL. Both antibodies displayed reactivity for the 150 kDa band (not shown). To confirm that the bivalent assembly was functional, a phage enzyme-linked immunosorbent assay (ELISA) was performed against the protein target vascular endothelial growth factor (VEGF). This antibody was matured against VEGF in a similar bivalent format [21, 30]. As shown in FIG. 3D, a strong specific binding signal for biotinylated VEGF immobilized to a streptavidin-coated surface was observed.

Figures 4A, 4B:
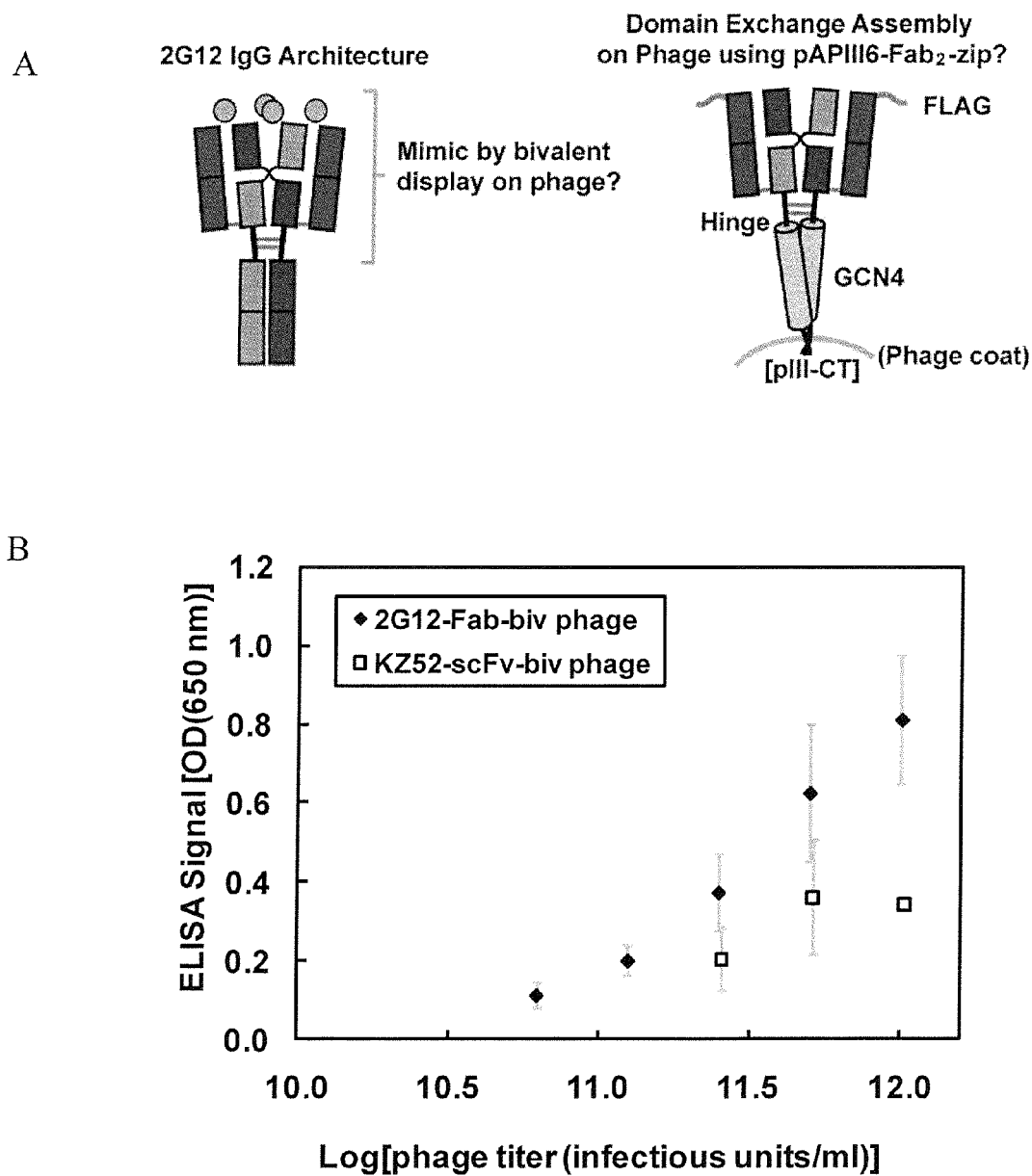
FIG. 4A-4B. Bivalent display of functional 2G12 dimer. (A) Schematic for mimicking the domain-exchange dimer on the surface of phage using pAPIII6-Fab$_2$-zip. (B) Phage ELISA of 2G12-Fab-biv phage or KZ52-scFv-phage for binding wells coated with HIV-1 pseudovirus.

DNA encoding 2G12 VL and VH fragments was cloned into the respective open reading frames of a bivalent display vector. It was hypothesized that the bivalent nature of the display would allow for VH-VH' domain exchange on the surface of phage (FIG. 4A) to result in functionally displayed 2G12. To determine if the display 2G12 was functional, phage ELISA was performed of bivalent 2G12-displaying phage particles ('2G12-Fab-biv phage') against wells coated with immobilized HIV-1 pseudovirus, which bears the highly glycosylated gp120 on its surface. As shown in FIG. 4B, a phage-dependent binding signal was observed for 2G12-Fab-biv phage. A control phage displaying an unrelated single-chain variable fragment (scFv) in a similar bivalent format ('KZ52-scFv-biv phage') did show some non-specific binding signal for the HIV-1 pseudovirus. However, the KZ52-scFv-biv phage binding signal was much lower than that of 2G12-Fab-biv phage at higher phage titers. Together, these results indicate that 2G12 is expressed functionally on the surface of 2G12-Fab-biv phage.

Figures 5A, 5B:
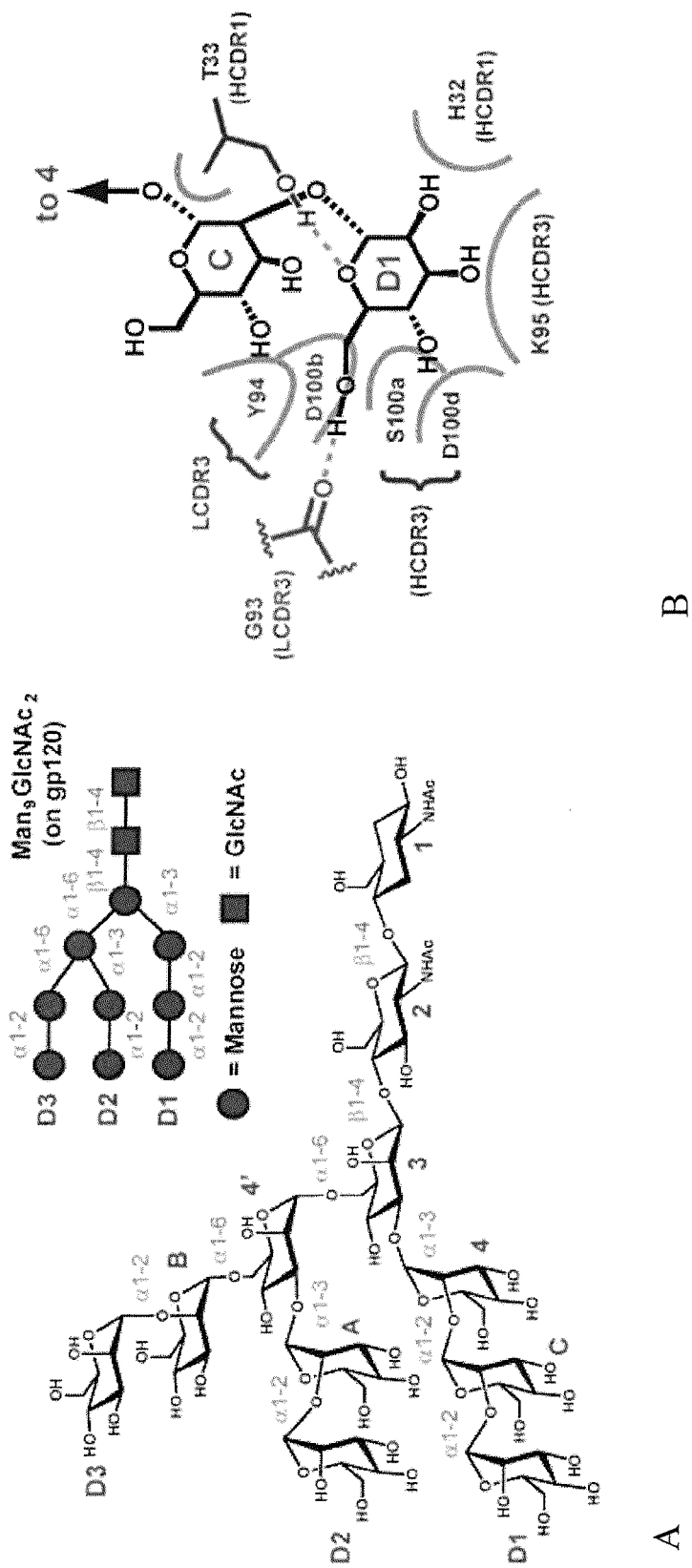
FIG. 5A-5B. (A) Chemical structure of Man$_9$GlcNAc$_2$, the natural target of 2G12. (B) Contact analysis in the primary combining site of 2G12. Residues from VL are in upper right (G93, LCDR3, Y94, D100b). Other residues are from VH.

Residues biased toward high-affinity protein-glycan interactions: A close examination of the 2G12 primary combining site reveals that contacts with the D1 and C mannose residues of $Man_9GlcNAc_2$ (the natural 2G12 target, FIG. 5A) are mediated primarily by van der Waals contacts (FIG. 5B) [25]. Surprisingly, only two hydrogen bonds stabilize the interaction: one between the β-hydroxyl of T33 in HCDR1 and the ring oxygen of the D1 mannose; and another involving the backbone carbonyl of G93 in LCDR3 and the C6' hydroxyl of the D1 mannose. Residues H32, K95, S100a, and D100d (of the heavy chain) line the lower boundary of the pocket. A 'clamp' over the D1 mannose is formed by Y94 and D100b of LCDR3. Contact analysis of the secondary site is less straightforward since this site does not form a distinct glycan-binding pocket, but residues R28, L74, E75, and D76 of VH form direct contacts with the glycan. Minimal residue subsets could be identified that are biased toward glycan interactions at these positions in the 2G12 scaffold.

To determine if the 2G12 (Fab)2 fragment was efficiently expressed, phage particles were prepared from p2G12-(Fab)2zip using standard procedures. These phage particles were subjected to Western blot analysis using a FLAG epitope on the light chain for detection (FIG. 6A). A band was observed that corresponded to ~150 kDa assembly under non-reducing conditions, the expected molecular weight of the 2G12 (Fab)2-hinge-GCN4-pIII assembly. When the phage were subjected to non-reducing conditions, a band of ~25 kDa was observed, which corresponds to the unassembled light chain. These results indicate that the bivalent (Fab)2 assembly is expressed on the surface of phage. Phage ELISA was performed to determine if the 2G12 (Fab)2 fragment was functional. A strong ELISA signal for binding of phage particles produced from p2G12-(Fab)2zip to wells coated with gp120 was observed but not BSA, and this binding signal was phage titer-dependent (FIG. 6B). Furthermore, the phage particles exhibited similar phage-dependent binding to wells coated with anti-idiotype antibody M1G1, which binds to 2G12 in a manner that is dependent on the domain exchange. Importantly, a control phage expressing the scFv of an irrelevant antibody (KZ52) did not exhibit binding to either gp120 or M1G1. These data indicate that the 2G12(Fab)2 fragment is properly assembled, since the binding to both gp120 and M1G1 is dependent on proper functional domain exchange.

To further explore the dependency of sensitivity of the ELISA assay for functional domain exchange, several site-specific mutants of p2G12-Fab2zip were created. Three residues have previously been identified at the VH-VH' interface that are critical for stabilizing the domain exchange (I19, F77, and Y79A). A triple mutant of p2G12-Fab2zip was prepared in which each of these positions was altered to alanine (I19A/F77A/Y79A, p2G12-TriMut). In addition, the crystal structure of the 2G12 Fab in complex with oligomannose revealed several positions in HCDR1 and HCDR3 that participate in antigen-binding contacts. Three additional variants were created in which a total of nine positions in these regions were altered from WT to Ala (p2G12-Ala), Gly (p2G12-Gly), or Arg (p2G12-Arg). These mutations are expected to be deleterious to glycan binding. The binding of each of these clones to immobilized gp120 was compared by phage ELISA (FIG. 7). Since the mutants may exhibit differential display properties relative to WT, a phage ELISA was also performed that would allow evaluation of the expression against anti-FLAG antibody M2. The functional ELISA (gp120) was performed at phage titers in which similar signals for binding to antibody M2 were observed; this should provide a direct comparison of the binding capacity for the expressed fragments irrespective of any differences in display. The WT 2G12 clone (p2G12-Fab2-zip) bound with much strong binding signal than did the domain interface triple mutant (p2G12-TriMut), or clones in which the contact HCDR1 and HCDR3 contact residues had been altered (p2G12-Ala, p2G12-Gly, and p2G12-Arg). These results further indicate that the 2G12 domain exchange is functional.

To test the capacity of the p2G12-Fab2zip system for selection of functional selection, mixtures of phage populations were prepared containing p2G12-Ala, p2G12-Gly, or p2G12-Arg spiked with p2G12-Fab2zip. In theory, if the bivalent p2G12-Fab2zip was amenable to selection of high affinity clones, then the amount of the WT 2G12 clone (p2G12-Fab2zip) should be enriched relative to the less functional mutant clones. Various mixtures of p2G12-Ala, p2G12-Gly, or p2G12-Arg and p2G12-Fab2zip were prepared (Table 2) and subjected to selection against immobilized gp120. As expected, enrichment was observed detected by both output titers relative to control wells containing BSA and frequency of p2G12-Fab2zip clones.

Library Production

Libraries can be produced using a method known as Kunkel mutagenesis. 'Template DNA' can be extracted from phage particles using a commercial kit (QIAgen). This template DNA can be produced in such a way that it can be easily degraded by electroporation into a suitable host. Regions of randomization can be incorporated (to produce library DNA) by oligonucleotide-directed DNA synthesis in which the oligonucleotides contain designed segments of randomization. This can be accomplished by mixing the template DNA, the oligonucleotide primers, the enzymes T4 ligase and T4 or T7 polymerase, and all other necessary DNA synthesis reagents overnight. The library DNA can then be purified and electroporated into *E. coli* XL1-Blue, which will preferentially degrade any leftover template DNA. Phage can be produced from these cells (as above) and harvested (as above). These phage will constitute the library.

Though much less structural information exists for glycan-protein interactions than for protein-protein or protein-nucleic acid interactions, a survey of known structures provided a rough template to design the codon sets listed in Table 1 [6, 7, 14-17]. Similar to protein-protein interfaces, glycan-protein interfaces appear to be enriched in Tyr residues; however, Asn and Gln appear to play important roles in glycan recognition as well. It was hypothesized that, since glycans contain many polar hydroxyl groups, glycan-binding sites are enriched in these residues that can participate in dipole-dipole (e.g., van der Waals) interactions or hydrogen bonds. Stacking interactions between aromatic groups and the sugar rings appears to be another common feature. Charged residues were less frequently involved in direct glycan contacts, likely because most sugars have no ionic groups, but in some cases acidic groups were involved in the interaction. Based on this survey, a series of codon sets was designed as shown in Table 1. Each successive codon sets from the top of Table 1 to the bottom contains residues with fewer physicochemical properties. The right most column of Table 1 shows the calculated maximum theoretical genetic diversity for 2G12-based libraries. 2G12 libraries can be screened against selected targets, such as for example, gp120 produced from CHO cells, the HIV-1 pseudovirus, or the $Le^Y$ antigen. $Le^Y$ is a therapeutically relevant target since it is highly expressed in many cancer cell lines [6, 7]. A $Le^Y$ antibody-drug conjugate is currently under evaluation as a targeted therapy [10]. Related antigens sialyl Lewis X and Lewis X are also thought to play significant roles in infection by *Helicobacter pylori*, therefore any antibodies directed at $Le^Y$ may also be useful for gastric diseases [6, 7].

Following rounds of selection against each target, the 'fitness' of each codon set can be determined by calculating the 'hit rate' against the target. At the end of the $4^{th}$ round, individual clones will be screened for their ability to bind their respective glycosylated target by high-throughput monoclonal phage ELISA, and the sequences of active clones determined. The 'hit rate' can be defined as [number of non-redundant clones exhibiting a specific binding signal for the target]/[total number of clones tested]. Clones that display the highest degree of binding and specificity will be expressed as bivalent Fabs. Thereby, one can determine the optimal minimal codon set for glycan-protein interactions.

TABLE 1

Degenerate Codons Used for 2G12-Based Library Design

| Codon[a] | Residues encoded | Comments | Diversity for 2G12-based library[b] |
|---|---|---|---|
| NNS | All 20 | Saturation mutagenesis | $32^{12} = 1 \times 10^{18}$ |
| DVK | A/C/D/E/G/K/N/R/S/T/W/Y | Aromatic, polar, and charged | $18^{12} = 1 \times 10^{15}$ |
| WNY | C/F/I/M/N/S/T/Y | Aromatic, hydrophobic, polar | $16^{12} = 3 \times 10^{14}$ |
| KVK | A/C/D/E/G/W/Y | Aromatic, polar, acidic[c] | $12^{12} = 9 \times 10^{12}$ |
| KMT | Y/A/D/S | Successful for protein antigens[d] | $4^{12} = 2 \times 10^{7}$ |
| TMT | Y/S | Successful for protein antigens[e] | $2^{12} = 4 \times 10^{3}$ |

[a]DNA degeneracies follow standard IUB nomenclature: N = A/T/C/G, S = G/C, D = A/G/T, V = A/C/G, K = G/T, W = A/T, Y = C/T, M = A/C.
[b]Maximum theoretical diversity is shown for a hypothetical 12-position library.
[c]Based on previous success with synthetic antibodies, acidic residues were focused on rather than basic residues.
[d]See ref. 21.
[e]See ref. 20.

REFERENCES

1. Prescher, J. A.; Bertozzi, C. R. Chemical Technologies for Probing Glycans. *Cell,* 2006, 126, 851-854.
2. Collins, B. E.; Paulson, J. C. Cell Surface Biology Mediated by Low Affinity Multivalent Protein-Glycan Interactions. *Curr. Opin. Chem. Biol.,* 2004, 8, 617-625.
3. van Kooyk, Y.; Rabinovich; G. A. Protein-Glycan Interactions in the Control of Innate and Adaptive Immune Responses. *Nat. Immunol.,* 2008, 9, 593-601.
4. Dam, T. K.; Brewer, C. F. Lectins as Pattern Recognition Molecules: The Effects of Epitope Density in Innate Immunity. *Glycobiology,* 2010, 20, 270-279.
5. Kaltgrad, E.; et al. Anti-Carbohydrate Antibodies Elicited by Polyvalent Display on a Viral Scaffold. *ChemBioChem,* 2007, 8, 1455-1462.
6. Jaffrey, P. D.; Bajorath, J.; Chang, C.-Y. Y.; Yelton, D.; Hellstrom, I.; Hellstrom, K. E.; Sheriff. The X-Ray Structure of an Anti-Tumor Antibody in Complex with Antigen. *Nat. Struct. Mol. Biol.,* 1995, 2, 466-471.
7. Van Roon, A.-M. M.; Pannu, N. S.; de Vrind, J. P. M.; van der Marel, G. A.; van Boom, J. H.; Hokke, C. H.; Deelder, A. M.; Abrahams, J. P. Structure of an Anti-Lewis X Fab Fragment in Complex with Its Lewis X Antigen. *Structure,* 2004, 12, 1227-1236.
8. Lee, J. H.; Park, S.-H.; Stanley, P. Antibodies that Recognize Bisected Complex N-Glycans on Cell Surface Glycoproteins Can Be Made in Mice Lacking N-Acetylglycosaminyltransferase III. *Glycoconj. J.,* 2003, 19, 211-219.
9. Rosok, M. H.; Yelton, D. E.; Harris, L. J.; Bajorath, J.; Hellstrom, K.-E.; Hellstrom, I.; Cruz, G. A.; Kristensson, K.; Lin, H.; Huse, W. D.; Glaser, S. M. A Combinatorial Library Strategy for the Rapid Humanization of Anticarcinoma BR96 Fab. *J. Biol. Chem.,* 1996, 271, 22611-22618.
10. Scott, A. M.; et al. Construction, Production, and Characterization of Humanized Anti-Lewis Y Monoclonal Antibody 3S193 for Targeted Immunotherapy of Solid Tumors. *Cancer Res.,* 2000, 60, 3254-3261.
11. Wang, C.-C.; Huang, Y.-L.; Ren, C.-T.; Lin, C.-W.; Hung, J.-T.; Yu, J.-C.; Yu, A. L.; Wu, C.-Y.; Wong, C.-H. Glycan Microarray of Globo H and Related Structures for Quantitative Analysis of Breast Cancer. *Proc. Natl. Acad. Sci. USA,* 2008, 105, 11661-11666.
12. Pilobello, K. T.; Mahal, L. K. Deciphering the Glycocode: The Complexity and Analytical Challenge of Glycomics. *Curr. Opin. Chem. Biol.,* 2007, 11, 300-305.
13. Danishefsky, S. J.; Allen, J. R. From the Laboratory to the Clinic: A Retrospective on Fully Synthetic Carbohydrate-Based Anticancer Vaccines. *Angew. Chem. Intl. Ed.,* 2000, 39, 836-863.
14. Kitamura, K.; Stockert, E.; Garin-Chesa, P.; Welt, S.; Lloyd, K. O.; Armour, K. L.; Wallace, T. P.; Harris, W. J.; Carr, F. J.; Old, L. J. Specificity Analysis of Blood Group Lewis-Y (LeY) Antibodies Generated Against Synthetic

TABLE 2

Sequence analysis from mock selection.

| Input phage mixture | Input titer | Output titer (gp120) | Output titer (BSA) | Frequency of WT in input population[a] | Frequency of WT in output population[a] |
|---|---|---|---|---|---|
| p2G12-Fab$_2$zip/p2G12-Ala | $6 \times 10^9$ | $2 \times 10^6$ | $1 \times 10^5$ | 27/94 (29%) | 62/94 (66%) |
| | $3 \times 10^{12}$ | $8 \times 10^7$ | $5 \times 10^7$ | 2/94 (2%) | 14/94 (15%) |
| p2G12-Fab$_2$zip/p2G12-Gly | $2 \times 10^{10}$ | $2 \times 10^6$ | $2 \times 10^5$ | 3/94 (2%) | 20/94 (21%) |
| p2G12-Fab$_2$zip/p2G12-Arg | $4 \times 10^{10}$ | $2 \times 10^6$ | $1 \times 10^5$ | 0/94 (0%) | 10/94 (11%) | and Natural LeY Determinants. *Proc. Natl. Acad. Sci. USA,* 1994, 91, 12957-12961.
15. Zdanov, A.; Li, Y.; Bundle, D. R.; Deng, S. J.; MacKenzie, C. R.; Narang, S. A.; Young, N. M.; Cygler, M. Structure of a Single-Chain Antibody Variable Domain Fragment (Fv) Complexed with a Carbohydrate Antigen at 1.7 Å Resolution. *Proc. Natl. Acad. Sci. USA,* 1994, 91, 6423-6427.
16. Villeneuve, S.; Souchon, H.; Riottot, M. M.; Mazie, J. C.; Lei, P.; Glaudemans, C. P.; Kovac, P.; Fournier, J. M.; Alzari, P. M. Crystal Structure of an Anti-Carbohydrate Antibody Directed against *Vibrio cholera* O1 in Complex with Antigen: Molecular Basis for Serotype Specificity. *Proc. Natl. Acad. Sci. USA,* 2000, 97, 8433-8438.
17. Nguyen, H. P.; Seto, N. O. L.; MacKenzie, C. R.; Brade, L.; Kosma, P.; Brade, H.; Evans, S. V. Germline Antibody Recognition of Distinct Carbohydrate Epitopes. *Nat. Struct Biol.,* 2003, 10, 1019-1025.
18. Sidhu, S. S.; Fellouse, F. A. Synthetic Therapeutic Antibodies. Nat. Chem. Biol., 2006, 2, 682-688.
19. Sidhu, S. S.; Li, B.; Chen, Y.; Fellouse, F. A.; Eigenbrot, C.; Fuh, G. Phage-Dislayed Antibody Libraries of Synthetic Heavy Chain Complementarity Determining Regions. *J. Mol. Biol.,* 2004, 338, 299-310.
20. Fellouse, F. A.; Li, B.; Campaan, D. M.; Peden, A. A.; Hymowitz, S. G.; Sidhu, S. S. Molecular Recognition by a Binary Code. *J. Mol. Biol.,* 2005, 348, 1153-1162.
21. Fellouse, F. A.; Weismann, C.; Sidhu, S. S. Synthetic Antibodies from a Four-Amino Acid Code: A Dominant Role of Tyrosine in Antigen Recognition. *Proc. Natl. Acad. Sci. USA,* 2004, 101, 12467-12472.
22. Barbas, C. F.; Bain, J. D.; Hoekstra, D. M.; Lerner, R. A. Semisynthetic Combinatorial Antibody Libraries: A Chemical Solution to the Diversity Problem. *Proc. Natl. Acad. Sci. USA,* 1992, 89, 4457-4461.
23. Cobaugh, C. W.; Almagro, J. C.; Pogson, M.; Iverson, B.; Georgiou, G. Synthetic Antibody Libraries Focused Towards Peptide Ligands. *J. Mol. Biol.,* 2008, 378, 622-633.
24. Fellouse, F. A.; Esaki, K.; Birtalan, S.; Raptis, D.; Cancasci, V. J.; Koide, A.; Jhurani, P.; Vasser, M.; Wiesmann, C.; Kossiakoff, A. A.; Koide, S.; Sidhu, S. S. High-Throughput Generation of Synthetic Antibodies from Highly Functional Minimalist Phage-Displayed Libraries. *J. Mol. Biol.,* 2007, 373, 924-940.
25. Calarese, D. A.; Scanlan, C. N.; Zwick, M. B.; Deechongkit, S.; Mimura, Y.; Kunert, R.; Ping, Z.; Wormald, M. R.; Stanfield, R. L.; Roux, K. H.; Kelly, J. W.; Rudd, P. M.; Dwek, R. A.; Katinger, H.; Burton, D. R.; Wilson, I. A. Antibody Domain Exchange Is an Immunological Solution to Carbohydrate Cluster Recognition. *Science,* 2003, 300, 2065-2071.
26. Calarese, D. A.; Lee, H. K.; Huang, C. Y.; Best, M. D.; Astronomo, R. D.; Stanfield, R. L.; Katinger, H.; Burton, D. R.; Wong, C. H.; Wilson, I. A. Dissection of the Carbohydrate Specificity of the Broadly Neutralizing Anti-HIV-1 Antibody 2G12. *Proc. Natl. Acad. Sci. USA,* 2005, 102, 13372-13377.
27. Wang, L.-X.; Ni, J.; Singh, S.; Li, H. Binding of High-Mannose-Type Oligosaccharides and Synthetic Oligomannose Clusters to Human Antibody 2G12: Implications for HIV-1 Vaccine Design. *Chem. Biol.,* 2004, 11, 127-134.
28. *Phage Display: A Practical Approach.* Clackson, T.; Lowman, H. B., Eds. Oxford University Press: New York, N.Y., 2004. pp. 27-41.
29. Haidaris, C. G.; Malone, J.; Sherrill, L. A.; Bliss, J. M.; Gaspari, A. A.; Insel, R. A.; Sullivan, M. A. Recombinant Human Antibody Single Chain Variable Fragments Reactive with *Candida Albicans* Surface Antigents. *J. Immunol. Methods,* 2001, 257, 185-202.
30. Lee, C. V.; Sidhu, S. S.; Fuh, G. Bivalent Antibody Phage Display Mimics Natural Immunoglobulin. *J. Immunol. Methods,* 2004, 284, 119-132.

---

What is claimed is:

1. A nucleic acid construct comprising HindIII (AAGCTT), 2G12 VL (SEQ ID NO:1), $C_L$ (SEQ ID NO:2), Intragenic region (SEQ ID NO:3), pel B (SEQ ID NO:4), Region X (SEQ ID 5), spe I (ACTAGT), VH (SEQ ID NO:6), $C_H$ (SEQ ID NO:7), Hinge (SEQ ID NO:8), GCN4 (SEQ ID NO:9), and SalI (GTCGAC), or a modified version thereof wherein the modification consists of one or more modification in the sequence of the 2G12 VL region and/or one or more modification in the sequence of the VH region, and wherein the modification consists of a substitution of one codon for another codon, up to nine such substitutions, and/or insertion of up to nine additional codons.

2. The nucleic acid construct of claim 1, comprising one or more modification in the sequence of the 2G12 VL region.

3. The nucleic acid construct of claim 2, comprising a modification in the "TAC" nucleotides at nucleotide positions 277-279 of SEQ ID NO:1.

4. The nucleic acid construct of claim 1, comprising one or more modification in the sequence of the VH region.

5. The nucleic acid construct of claim 4, comprising a modification in one or more of the "CGT" nucleotides at nucleotide positions 81-83, the "CTGGAAGAC" nucleotides at nucleotide positions 223-231, and/or the GAC" nucleotides at nucleotide positions 316-318 of SEQ ID NO:6.

6. The nucleic acid construct of claim 1, comprising one or more modification in the sequence of the 2G12 VL region and one or more modification in the sequence of the VH region.

7. The nucleic acid construct of claim 1, wherein the codon that is added to, or substituted in, the sequence of the VL and/or VH region is selected from the group consisting of one or more of NNS, DVK, WNY, KVK, KMT and TMT.

8. A method for identifying an antibody that targets a glycan of interest, comprising:
   a) expressing an antibody encoded by the nucleic acid construct of claim 1 on the surface of bacteriophage; and
   b) contacting the bacteriophage with the glycan of interest;

wherein binding of the glycan to the antibody expressed on the bacteriophage identifies the antibody as an antibody that targets the glycan of interest, and wherein lack of binding of the glycan to the antibody expressed on the bacteriophage indicates that the antibody is not an antibody that targets the glycan of interest.

9. The method of claim 8, wherein the bacteriophage is a M13, fd filamentous phage, T4, T7 or λ bacteriophage.

10. The method of claim 8, wherein the glycan is immobilized to a fixed surface.

11. The method of claim 8, wherein the glycan of interest is oligomannose on HIV-1 gp120 or $Le^Y$ antigen.

12. The method of claim 8, wherein the antibody binds the glycan with a $K_D$ of 50 nM or lower.

\* \* \* \* \*

SEQUENCE LISTING

```
<160> NUMBER OF SEQ ID NOS: 9

<210> SEQ ID NO 1
<211> LENGTH: 321
<212> TYPE: DNA
<213> ORGANISM: Artificial Sequence
<220> FEATURE:
<223> OTHER INFORMATION: artificial sequence encodes VL

<400> SEQUENCE: 1
gttgttatga cccagtctcc gtctaccctg tctgcttctg ttggtgacac catcaccatc      60
acctgccgtg cttctcagtc tatcgaaacc tggctggctt ggtaccagca gaaacgggt     120 aaagctccga aactgctgat ctacaaagcg tctactctga aaaccggtgt tccgtctcgt     180
ttcagcggtt ctggttctgg tactgagttc accctgacca tctctggtct gcagttcgac     240
gacttcgcta cctaccactg ccagcactac gctggttact ctgctacctt cggccagggt     300
acccgtgtag aaatcaaacg t                                               321

<210> SEQ ID NO 2
<211> LENGTH: 321
<212> TYPE: DNA
<213> ORGANISM: Artificial Sequence
<220> FEATURE:
<223> OTHER INFORMATION: artificial sequence encodes CL
```

```
<400> SEQUENCE: 2
actgttgctg caccttctgt ctttatcttt cctccgtccg atgaacaatt gaagagcggc    60
acggcgtctg tggtttgcct gctgaataac ttttatccgc gtgaggcgaa ggtccaatgg   120
aaagttgata atgcgctgca aagcggtaac agccaagagt ctgtcaccga gcaagacagc   180
aaagacagca cctactctct gtccagcacc ctgacgctga gcaaagcaga ttacgagaaa   240
cataaggttt atgcatgtga agttacccac cagggtctga gcagcccggt taccaaatct   300
tttaaccgtg gtgagtgtta a                                              321

<210> SEQ ID NO 3
<211> LENGTH: 30
<212> TYPE: DNA
<213> ORGANISM: Artificial Sequence
<220> FEATURE:
<223> OTHER INFORMATION: Intragenic region

<400> SEQUENCE: 3
ttctagataa ttaattagga ggaatttaaa                                      30

<210> SEQ ID NO 4
<211> LENGTH: 63
<212> TYPE: DNA
<213> ORGANISM: Artificial Sequence
<220> FEATURE:
<223> OTHER INFORMATION: pel B

<400> SEQUENCE: 4
atgaaatacc tattgcctac ggcagccgct ggattgttat tactcgctgc ccaaccagcc    60
atg                                                                   63

<210> SEQ ID NO 5
<211> LENGTH: 15
<212> TYPE: DNA
<213> ORGANISM: Artificial Sequence
<220> FEATURE:
<223> OTHER INFORMATION: Region X

<400> SEQUENCE: 5
gccgaggtgc agctg                                                      15

<210> SEQ ID NO 6
<211> LENGTH: 369
<212> TYPE: DNA
<213> ORGANISM: Artificial Sequence
<220> FEATURE:
<223> OTHER INFORMATION: artificial sequence encodes VH

<400> SEQUENCE: 6
gaagttcagc tggttgaaag cggcggcggt ctggttaaag ctggcggttc tctgatcctg    60
tcttgcggtg tttctaactt ccgtatctct gctcacacca tgaactgggt tcgtcgtgtt   120
ccgggcggag gtctggaatg ggttgcttct atctctacct cttccaccta ccgtgactat   180
gctgacgctg ttaaaggtcg tttcaccgtt tctcgtgacg acctggaaga cttcgtttac   240
ctgcagatgc acaaaatgcg tgttgaagac accgctatct actactgcgc tcgtaaaggt   300
tctgaccgtc tgtctgacaa cgacccgttc gacgcttggg gtccgggcac cgttgttacc   360
gtaagcccg                                                            369
```

```
<210> SEQ ID NO 7
<211> LENGTH: 321
<212> TYPE: DNA
<213> ORGANISM: Artificial Sequence
<220> FEATURE:
<223> OTHER INFORMATION: artificial sequence encodes CH

<400> SEQUENCE: 7
gccagcacga aaggcccgag cgtgttcccg ctggcaccgt cgagcaaatc tacctccggt      60
ggcaccgcag ctctgggttg tctggttaag gactacttcc cggaacctgt taccgtgagc     120
tggaacagcg gtgcactgac ctctggtgtc cacaccttcc cagcagtgtt gcagagcagc     180
ggtctgtata gcctgagcag cgttgtgacg gttcctagca gcagcctggg tacgcagacc     240
tatatctgca acgtgaatca caagccgagc aacaccaaag ttgacaaaaa ggtcgagcca     300
aaaagctgtg ataaggagct c                                                321

<210> SEQ ID NO 8
<211> LENGTH: 36
<212> TYPE: DNA
<213> ORGANISM: Artificial Sequence
<220> FEATURE:
<223> OTHER INFORMATION: Hinge

<400> SEQUENCE: 8
acctgtccgc cttgccctgc gccggaactg ctgggc                                 36

<210> SEQ ID NO 9
<211> LENGTH: 102
<212> TYPE: DNA
<213> ORGANISM: Artificial Sequence
<220> FEATURE:
<223> OTHER INFORMATION: GCN4

<400> SEQUENCE: 9
ggtcgtatga aacaactgga ggacaaggtc gaggagttgt tgagcaagaa ctaccatctg      60
gagaacgaag tggcgcgtct gaagaaactg gttggtgaac gt                         102
```